United States Patent
Sekiguchi

(10) Patent No.: US 7,511,512 B2
(45) Date of Patent: Mar. 31, 2009

(54) PROBE AND NEAR-FIELD MICROSCOPE

(75) Inventor: Ryota Sekiguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 172 days.

(21) Appl. No.: 11/683,859

(22) Filed: Mar. 8, 2007

(65) Prior Publication Data
US 2007/0216422 A1 Sep. 20, 2007

(30) Foreign Application Priority Data
Mar. 17, 2006 (JP) ............................. 2006-073614

(51) Int. Cl.
- G01R 27/04 (2006.01)
- G01R 27/32 (2006.01)
- G01R 27/26 (2006.01)

(52) U.S. Cl. ...................... 324/638; 324/690
(58) Field of Classification Search ................ 324/638, 324/690
See application file for complete search history.

(56) References Cited

U.S. PATENT DOCUMENTS

| | | | | |
|---|---|---|---|---|
| 5,900,618 | A * | 5/1999 | Anlage et al. ............ | 250/201.3 |
| 6,597,185 | B1 | 7/2003 | Talanov et al. ............ | 324/638 |
| 6,680,617 | B2 | 1/2004 | Moreland et al. ........... | 324/638 |
| 6,856,140 | B2 | 2/2005 | Talanov et al. ............ | 324/638 |
| 6,943,562 | B2 * | 9/2005 | Talanov et al. ............ | 324/633 |
| 2004/0004484 | A1 | 1/2004 | Talanov et al. ............ | 324/633 |

FOREIGN PATENT DOCUMENTS

| JP | 2002-189043 | 7/2002 |
|---|---|---|
| JP | 2005-121422 | 5/2005 |

OTHER PUBLICATIONS

Wang et al., "Metal Wires for Terahertz Wave Guiding," *Nature*, vol. 432, 376-379 (2004).

* cited by examiner

Primary Examiner—Vincent Q Nguyen
Assistant Examiner—Amy He
(74) Attorney, Agent, or Firm—Fitzpatrick, Cella, Harper & Scinto

(57) ABSTRACT

A probe includes a tubular conductor having an aperture at one end thereof. An electromagnetic wave transmitting unit for transmitting an electromagnetic wave, via the tubular conductor, to a position distant from the aperture is disposed at one of the inside and the outside of the tubular conductor, and an electromagnetic wave receiving unit for receiving an electromagnetic wave, via the tubular conductor, from the position distant from the aperture is disposed in the other of the inside and the outside of the tubular conductor. The size of the aperture is smaller than or equal to the wavelength of the electromagnetic waves. The electromagnetic waves transmitted and received at the outside and the inside of the tubular conductor are coupled through the aperture. When an analyte to be observed is disposed so as to face the aperture, information of the analyte is obtained on the basis of a change in the coupling of the electromagnetic waves through the aperture.

8 Claims, 6 Drawing Sheets

PROBE AND NEAR-FIELD MICROSCOPE

BACKGROUND OF THE INVENTION

1. Field of the Invention

The present invention relates to a probe and a near-field microscope capable of obtaining information, such as dielectric properties, of an analyte using electromagnetic waves. More specifically, the present invention relates to a probe and a near-field microscope capable of observing physical properties, such as dielectric properties, of a minute region of an analyte using electromagnetic waves in the frequency region from the millimeter waveband to the terahertz band (30 GHz to 30 THz) (hereinafter also referred to as "high-frequency electrical signal").

2. Description of the Related Art

As a method for observing dielectric properties of a minute region of an analyte or a minute analyte, there is known a method in which the reflection of a high-frequency electrical signal from an analyte is measured using a high-frequency transmission line, such as a coaxial line or a high-frequency co-planar strip line, with a minute tip. This method is used in a wide frequency region from the microwave region to the visible region, and is called microwave probe (or microwave probe microscope) in the microwave region. Since a microwave probe uses a minute structure smaller than the wavelength, dielectric properties of a region smaller than the wavelength of the high-frequency electrical signal to be used can be measured. Therefore, the distribution of dielectric properties of an analyte can be imaged with high spatial resolution. In addition, the information of dielectric properties of an analyte can be read from the phase retardation and the decrease in amplitude of the high-frequency electrical signal reflected from the analyte. The phase retardation reflects the real part of the dielectric constant of the analyte, and the decrease in amplitude reflects the imaginary part of the dielectric constant of the analyte. Therefore, by analyzing these, dielectric properties of the analyte can be quantitatively evaluated.

Japanese Patent Laid-Open No. 2005-121422 discloses an apparatus that measures the complex dielectric constant of an analyte with a microwave probe according to the above-described principle. In the configuration of Japanese Patent Laid-Open No. 2005-121422, a generator transmits a high-frequency electrical signal to a coaxial line with a minute tip, and a reflected wave from an analyte is received by a detector via a directional coupler. In addition, it is also possible to provide a resonance structure of the high-frequency electrical signal in a high-frequency transmission line so as to make a high-frequency signal reflected from the analyte a standing wave, and to use a shift of resonance frequency or a change in resonator Q-value with the change in dielectric properties of the analyte, for imaging.

Japanese Patent Laid-Open No. 2002-189043 also discloses an apparatus that measures the complex dielectric constant of an analyte with a microwave probe according to the above-described principle. In the configuration of Japanese Patent Laid-Open No. 2002-189043, a generator transmits a high-frequency electrical signal to a multi-conductor transmission line with a minute tip via a first coupling probe, and a reflected wave from an analyte is received by a detector via a second coupling probe. By appropriately terminating the tip and the opposite end of the multi-conductor transmission line, the reflected wave from the analyte is made a standing wave in the multi-conductor transmission line.

The spatial resolution of these microwave probes is 1/1000 or less of the wavelength of the microwave. Therefore, they are so-called near-field probes (or near-field probe microscopes) in the visible region.

There are a variety of high-frequency transmission lines. Kanglin Wang, Daniel M. Mittleman: Nature, vol. 432 (2004) discloses a wire waveguide consisting of a single conductor. The wire waveguide features a capability of transmission of a high-frequency electrical signal across a comparatively wide frequency band. For example, it is known that its propagation loss is smaller than those of other multi-conductor high-frequency transmission lines in the frequency region from the millimeter waveband to the terahertz band, and its dispersion is also comparatively small.

However, in the microwave probe of the Japanese Patent Laid-Open No. 2005-121422, it is necessary to use a directional coupler or the like in order to branch the reflected wave of the high-frequency electrical signal from the analyte. This complicates the apparatus. In addition, in the frequency region from the millimeter waveband to the terahertz band, when the frequency of the high-frequency electrical signal to be used is high, the propagation loss in the high-frequency transmission line is not negligible. In the multi-conductor high-frequency transmission line as in Japanese Patent Laid-Open No. 2002-189043, the propagation loss is comparatively great, and therefore the sensitivity is low. Kanglin Wang, Daniel M. Mittleman: Nature, vol. 432 (2004) discloses only a wire waveguide consisting of a single conductor.

SUMMARY OF THE INVENTION

The present invention provides a probe and a near-field microscope with simple composition and high sensitivity.

In an aspect of the present invention, a probe includes a tubular conductor having an aperture at one end thereof; an electromagnetic wave transmitting unit for transmitting an electromagnetic wave, via the tubular conductor, to a position distant from the aperture; and, an electromagnetic wave receiving unit for receiving an electromagnetic wave, via the tubular conductor, from the position distant from the aperture. The electromagnetic wave transmitting unit is disposed at one of the inside and the outside of the tubular conductor, and the electromagnetic wave receiving unit is disposed at the other of the inside and the outside of the tubular conductor. The size of the aperture is smaller than or equal to the wavelength of the electromagnetic waves. The electromagnetic waves transmitted and received in the outside and the inside of the tubular conductor are coupled through the aperture. When an analyte to be observed is disposed so as to face the aperture, information of the analyte is obtained on the basis of a change in the coupling of the electromagnetic waves through the aperture. Typically, the electromagnetic waves used in this probe include part of the frequency region from 30 GHz to 30 THz.

In another aspect of the present invention, a near-field microscope includes the above-described probe and a position control system for controlling the relative positional relationship between the probe and the analyte.

In another aspect of the present invention, an analyte observing method for obtaining information of an analyte using the above-described probe or near-field microscope includes the step of making an electromagnetic wave that is a traveling wave or a standing wave exist in the inner part of the tubular conductor.

In the probe and the near-field microscope in the present invention, a tubular conductor serves as an electromagnetic wave transmission line. The inner part of the conductor is used as a waveguide, and the outer part of the conductor is used as a wire waveguide. Therefore, the tubular conductor in the present invention functions as two electromagnetic wave transmission lines, and the electromagnetic wave transmitted to an analyte can be separated from the electromagnetic wave reflected from the analyte. In order to separate these electromagnetic wave transmission lines, the conductor has a wall thickness sufficiently larger than the penetration depth into the conductor due to the skin effect of the electromagnetic wave. For example, in the case of a high-frequency electrical signal in the terahertz band, the tubular conductor has a wall thickness larger than or equal to a micron. At one end of such a tubular conductor, an aperture is formed. An analyte is disposed at the end of the tubular conductor, and the reflection of an electromagnetic wave from the analyte is measured. The analyte can be measured, for example, by transmitting an electromagnetic wave from a wire waveguide in the outer part of the conductor to the end of the conductor where the analyte is disposed, and guiding part of the electromagnetic wave reflected from the analyte to a waveguide in the inner part of the conductor.

Since the inner structure of the tubular conductor in the present invention is a waveguide, electromagnetic waves on the higher frequency side than the cutoff frequency can be transmitted. For example, in the case of a high-frequency electrical signal in the terahertz band, the inner diameter of the tubular conductor is at least 1 mm. Since the propagation loss in waveguides is generally smaller than those of other high-frequency transmission lines, the probe and the near-field microscope in the present invention have advantages. In addition, the operating frequency band of the probe and the near-field microscope according to the present invention is typically on the higher frequency side than the millimeter waveband. Therefore, the constraint due to the cutoff frequency of the waveguide does not matter for size reduction. For example, in the case where a high-frequency electrical signal in the millimeter waveband is used, the inner diameter of the waveguide is at most a few millimeters.

Since the outer part of the tubular conductor in the present invention is a wire waveguide, a high-frequency electrical signal can be transmitted across a wide frequency band. It is known that, as shown in Kanglin Wang, Daniel M. Mittleman: Nature, vol. 432 (2004), the conductor loss in a wire waveguide is small particularly in the frequency region from the millimeter waveband to the terahertz band, and a wire waveguide is superior to other multi-conductor high-frequency transmission lines. Therefore, this point is also an advantage of the probe and the near-field microscope in the present invention. Even in a wire waveguide whose length in the transmission direction is more than a dozen centimeters, the loss and dispersion of the high-frequency electrical signal is comparatively small and hardly matters. However, the conductor loss of the conductor increases with the increase in frequency of the high-frequency electrical signal. Therefore, the upper limit of the frequency at which the propagation loss of a wire waveguide is no longer negligible is estimated at several tens of terahertz.

In the present invention, the above-described two electromagnetic wave transmission lines inside and outside the conductor are terminated at the position of the aperture at the tip of the conductor and are coupled with each other through the aperture. Therefore, for example, when an analyte is located at a distance of about the size of the minute aperture from the tip, the change in the dielectric properties of the analyte gives a change in the efficiency of the coupling. Therefore, typically, the dielectric information of the analyte can be read by measuring the high-frequency electrical signal passing through the minute aperture. In other words, with the change in the dielectric properties of the analyte, the impedance at the common terminal end of the two electromagnetic wave transmission lines inside and outside the conductor changes. Therefore, the amplitude and phase of the reflected wave from one electromagnetic wave transmission line to the other electromagnetic wave transmission line change. By analyzing these, the dielectric properties of the analyte can be evaluated. Since such an evaluation is useful typically for obtaining a spatial resolution smaller than or equal to the electromagnetic wave, the size of the minute aperture is smaller than or equal to the wavelength. For example, in the case of a high-frequency electrical signal in the terahertz band, the size of the minute aperture is smaller than or equal to 1 mm. The size of the minute aperture may be changed according to the spatial resolution of the desired dielectric information of the analyte.

The electromagnetic wave used in the present invention is transmitted by a generator that is an appropriate electromagnetic wave transmitting unit, and is received by a detector that is an appropriate electromagnetic wave receiving unit. As described above, in order to provide the reflection from one electromagnetic wave to the other electromagnetic wave, it is most simple to dispose the generator outside the tubular conductor and to dispose the detector inside the tubular conductor. Alternatively, the generator may be disposed inside the tubular conductor and the detector may be disposed outside the tubular conductor. By just determining the positional relationship between the generator and the detector as above, the need for a directional coupler is eliminated. According to the present invention, since a tubular conductor is used as a waveguide and a wire waveguide, a probe and a near-field microscope that require no directional coupler can be provided, and the apparatus can be made comparatively simple. In addition, since the propagation loss in the millimeter waveband to the terahertz band can be reduced, the sensitivity of the probe and the near-field microscope can be made comparatively high.

Further features of the present invention will become apparent from the following description of exemplary embodiments (with reference to the attached drawings).

DESCRIPTION OF THE EMBODIMENTS

An embodiment of the present invention will now be described with reference to the drawings. The embodiment of a probe and a near-field microscope includes a high-frequency transmission line that is a tubular conductor having a minute aperture at the tip thereof, and a generator and a detector respectively generating and detecting a high-frequency electrical signal including part of the frequency region from 30 GHz to 30 THz for measuring characteristics of an analyte.

Figure 1:
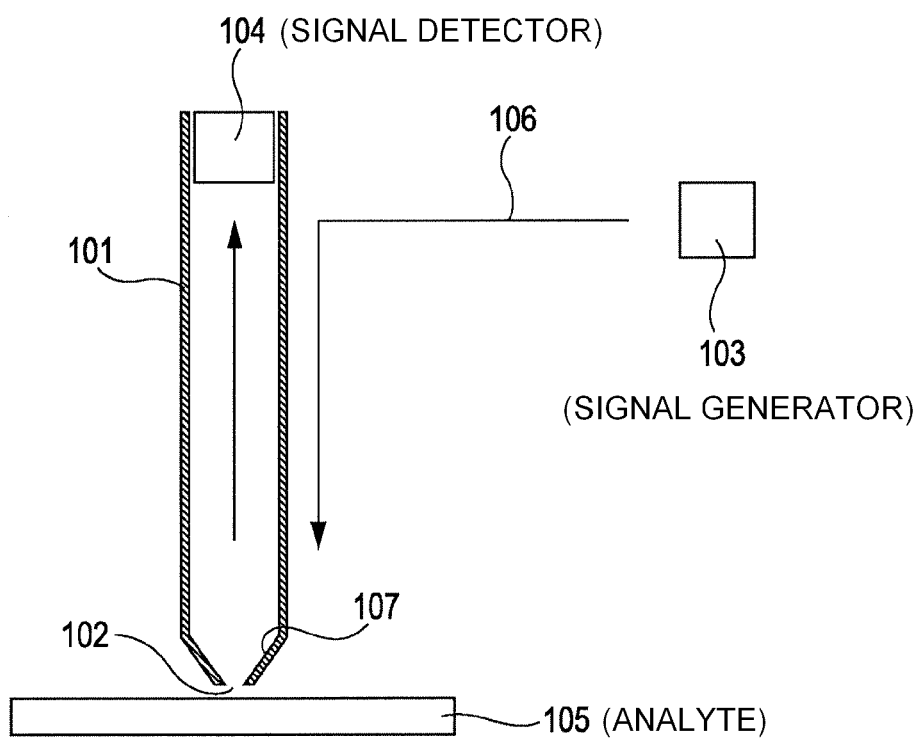
FIG. 1 is a sectional view showing the schematic configuration of an embodiment of the present invention.

FIG. 1 is a sectional view showing the configuration of a probe and a near-field microscope in this embodiment. In FIG. 1, reference numeral 101 denotes a tubular conductor, and reference numeral 102 denotes a minute aperture formed at the terminal end of the tubular conductor 101. The size of the minute aperture 102 is smaller than or equal to the wavelength of the electromagnetic wave of the high-frequency electrical signal. The tubular conductor 101 is, for example, a circular waveguide or a rectangular waveguide. The inner diameter of the tubular conductor 101 is, for example, about the wavelength of the electromagnetic wave. The wall thickness of the tubular conductor 101 is extremely thinner than the inner diameter thereof, for example, about the skin depth of the electromagnetic wave. An analyte 105 to be measured is disposed near the minute aperture 102.

Reference numeral 103 denotes a high-frequency electrical signal generator. In this embodiment, it is disposed outside the tubular conductor 101. Reference numeral 104 denotes a high-frequency electrical signal detector. In this embodiment, it is disposed inside the tubular conductor 101. Reference numeral 106 shown by arrows outside and inside the tubular conductor 101 denotes a propagation path of the high-frequency electrical signal due to the foregoing arrangement.

The propagation path 106 of the high-frequency electrical signal will be described. Part of the high-frequency electrical signal transmitted from the generator 103 is caught by the tubular conductor 101. At this time, as shown in FIG. 1, the high-frequency electrical signal propagates through the outer part of the tubular conductor 101 (functioning as a wire waveguide) and reaches near the minute aperture 102. Part of the high-frequency electrical signal reflected by the analyte 105 passes through the minute aperture 102, propagates through the inner part of the tubular conductor 101 (functioning as a waveguide) as shown in FIG. 1, reaches the detector 104, and is detected therein. In this way, the reflection of the high-frequency electrical signal from the analyte 105 is measured.

In FIG. 1, the tubular conductor 101 is provided with a taper structure 107 at the tip thereof in order to make the minute aperture 102 smaller so as to obtain a higher resolution, and in order to improve the efficiency of the propagation in the two high-frequency transmission lines inside and outside the conductor 101, which are coupled via the minute aperture 102. The taper structure 107 may be a multistage taper structure. The minute aperture 102 may be circular or rectangular. The size of the aperture, which provides the spatial solution, is preferably nearly equal to the spatial frequency of the dielectric properties of the analyte or the size of the minute region of the analyte. In order to efficiently couple the high-frequency electrical signal transmitted from the generator 103 to the tubular conductor 101, the high-frequency electrical signal may be appropriately collected with an optical device such as a lens, and the tubular conductor 101 may be irradiated therewith.

In this embodiment, the high-frequency electrical signal obtained in the detector 104 can be separated as follows. That is to say, the high-frequency electrical signal passing through the minute aperture 102 can be separated into the high-frequency electrical signal that is not related to the presence or absence of the analyte 105 and the high-frequency electrical signal that is so related. The proportion of these is the contrast obtained in the detector 104. The high-frequency electrical signal that is related to the presence or absence of the analyte 105, that is to say, the reflection from the analyte depends on the distance between the minute aperture 102 and the analyte 105, the complex dielectric constant of the analyte 105, and the shape of the analyte 105. Therefore, for example, if scanning is performed with the distance between the minute aperture 102 and the analyte 105 maintained constant, an image according to the complex dielectric constant distribution of the skin structure of the analyte 105 can be obtained. In this case, when the distance between the minute aperture 102 and the analyte 105 is nearly equal to the size of the minute aperture 102, an excellent contrast is obtained. The information thus obtained in the detector 104, such as the phase retardation and the amplitude of the high-frequency electrical signal, is sent to a PC (not shown) and analyzed.

The high-frequency electrical signal transmitter 103 is selected according to, for example, the frequency region of the complex dielectric constant of the analyte to be observed. If the frequency region is the millimeter waveband or the submillimeter waveband, it may be a Gunn oscillator using a Gunn diode. In this case, the high-frequency electrical signal detector 103 may be a Schottky barrier diode for detection. If the frequency region is the terahertz band, photoconductive antennas can be used as the transmitter and the detector. The transmitter may also be a BWO (Backward Wave Oscillator), a quantum cascade laser, or a resonant tunneling diode, and the detector may also be a pyroelectric element or a Golay cell.

In accordance with the purpose of the invention, the outer-wall structure of the tubular conductor can have a dielectric coating for reducing the propagation loss of the high-frequency electrical signal. Although the inside of the tubular conductor is preferably hollow (that is to say, air) from the viewpoint of efficient electromagnetic wave propagation, the inner structure of the above-described tubular conductor may be filled with a dielectric material having a small dielectric tangent. The dielectric tangent (tan δ) of the dielectric material is preferably 0.1 or less. In this case, manufacturing is easy, and the size can be reduced to be several times smaller. In addition, a high-frequency electrical signal coupling unit, such as a cross wire, may be disposed in the outer structure of the tubular conductor. This is used when the high-frequency electrical signal generator or the high-frequency electrical signal detector is located in a free space, in order to reduce the frequency dependency of the efficiency of coupling the outer structure (wire waveguide) of the tubular conductor and the free space, or in order to improve the coupling efficiency itself for a particular frequency.

EXAMPLES

Examples of specific configurations are as follows.

First Example

Figure 2:
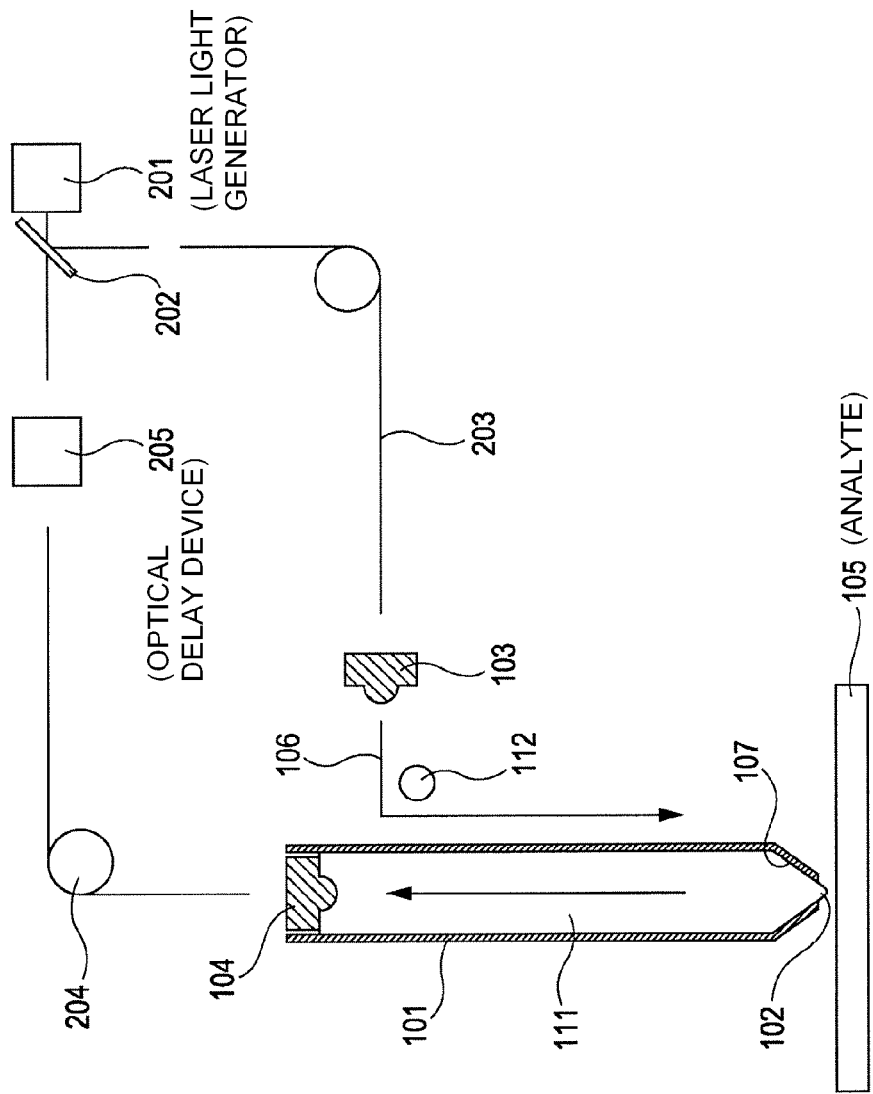
FIG. 2 is a sectional view showing the configuration of a probe and a near-field microscope according to a first example of the present invention.

FIG. 2 is a sectional view showing a first example of a probe and a near-field microscope according to the present invention. In FIG. 2, reference numeral 101 denotes a circular waveguide filled with a dielectric material 111, and reference numeral 102 denotes a minute aperture at the terminal end of the circular waveguide 101. Also in this case, as described above, an analyte 105 is disposed near the minute aperture 102.

Reference numeral 103 denotes a terahertz wave generator, which in this example is a photoconductive antenna. Reference numeral 104 denotes a terahertz wave detector, which is also a photoconductive antenna. Reference numeral 107 denotes a taper structure formed at the tip of the circular waveguide 101. Reference numeral 106 denotes the flow of the terahertz wave due to the arrangement of the above elements.

In this example, the inner diameter of the circular waveguide 101 is 1 mm, and the dielectric material 111 is Teflon (registered trade name), whose dielectric constant is about 2, and whose dielectric tangent (tan δ) is comparatively small. Therefore, the cutoff frequency of the circular waveguide 101 in the TE11 mode is calculated at about 0.12 THz, and most of the frequency region (0.1 THz or more) of the terahertz wave generated from a typical photoconductive antenna can be used.

As in this example, in order to obtain the information of both the phase retardation and the amplitude of the terahertz wave in the detector 104, an optical delay device 205 and a beam splitter 202 may be provided. That is to say, a configuration including a delay device or a heterodyne detector for measuring the phase difference between the reflected wave from the analyte and the original high-frequency electrical signal can be selected.

In this case, a femtosecond laser light generator 201 injects light into the terahertz wave generator 103 and the terahertz wave detector 104 via optical fibers 203 and 204, respectively. Since the terahertz wave radiated from the terahertz wave generator 103 is comparatively broadband, if a cross-wire terahertz wave coupling unit 112 disclosed in Nature, vol. 432 (2004) is used, the coupling efficiency will be flat in a comparatively wide frequency region. This coupling unit 112 is, for example, a metal wire extending in the direction perpendicular to the plane of FIG. 2.

This example operates, for example, as follows. The distance between the minute aperture 102 side end and the detector 104 side end of the circular waveguide 101 is, for example, 3 mm or more. The resonance frequency of the circular waveguide 101 in the vertical direction in FIG. 2 is smaller than the product of the frequency of the terahertz wave to be used and 1/Q (Q is the resonator Q value) of the circular waveguide resonator. In this case, the reflection of the terahertz wave from the analyte 105 negligibly produces a standing wave. In this way, information such as the phase retardation (the imaginary part of the dielectric constant) and the amplitude (the real part of the dielectric constant) of the reflected wave with the dielectric properties of the analyte 105 can be measured as the dielectric properties of the analyte 105 in a comparatively wide frequency region. That is to say, when information of the analyte is obtained using the above probe or near-field microscope, the information of the analyte can be obtained by making an electromagnetic wave that is a traveling wave exist in the inner part of the tubular conductor.

Alternatively, if the distance between the minute aperture 102 side end and the detector 104 side end of the circular waveguide 101 is, for example, about 3 mm, the resonance frequency of the circular waveguide 101 in the vertical direction in FIG. 2 appears about every 35 GHz. Therefore, peaks are detected at every integral multiple of this value. The dielectric properties of the analyte changes the resonator Q value or shifts the resonance frequency. Therefore, this method may be used to measure the dielectric properties of the analyte 105 at a particular frequency. Thus, when information of the analyte is obtained using the above probe or near-field microscope, the information of the analyte can also be obtained by making an electromagnetic wave that is a standing wave exist in the inner part of the tubular conductor.

In this example, the circular waveguide 101 filled with the dielectric material 111 is manufactured so that the tip of a Teflon tube of 1.0 mm in diameter is dissolved by chemical etching so as to be sharpened. Next, the Teflon tube is coated by vapor deposition with, for example, gold. The coating may be silver, copper, aluminum, brass, or nickel. The skin depth for gold of the terahertz wave used in this example is several tens of nanometers to several hundred nanometers. Therefore, coupling of the two high-frequency transmission lines inside and outside the circular waveguide 101 can be prevented with a submicron film thickness (for example, 300 nm). In addition, in order to make the minute aperture 102, the tip is cut, and chemical etching is performed. To the other end of the thus made circular waveguide 101 filled with the dielectric material 111, a photoconductive antenna functioning as the terahertz wave detector 104 is attached, for example, with an epoxy adhesive. The probe according to this example can be manufactured, for example, through the above well-known process.

Figure 5:
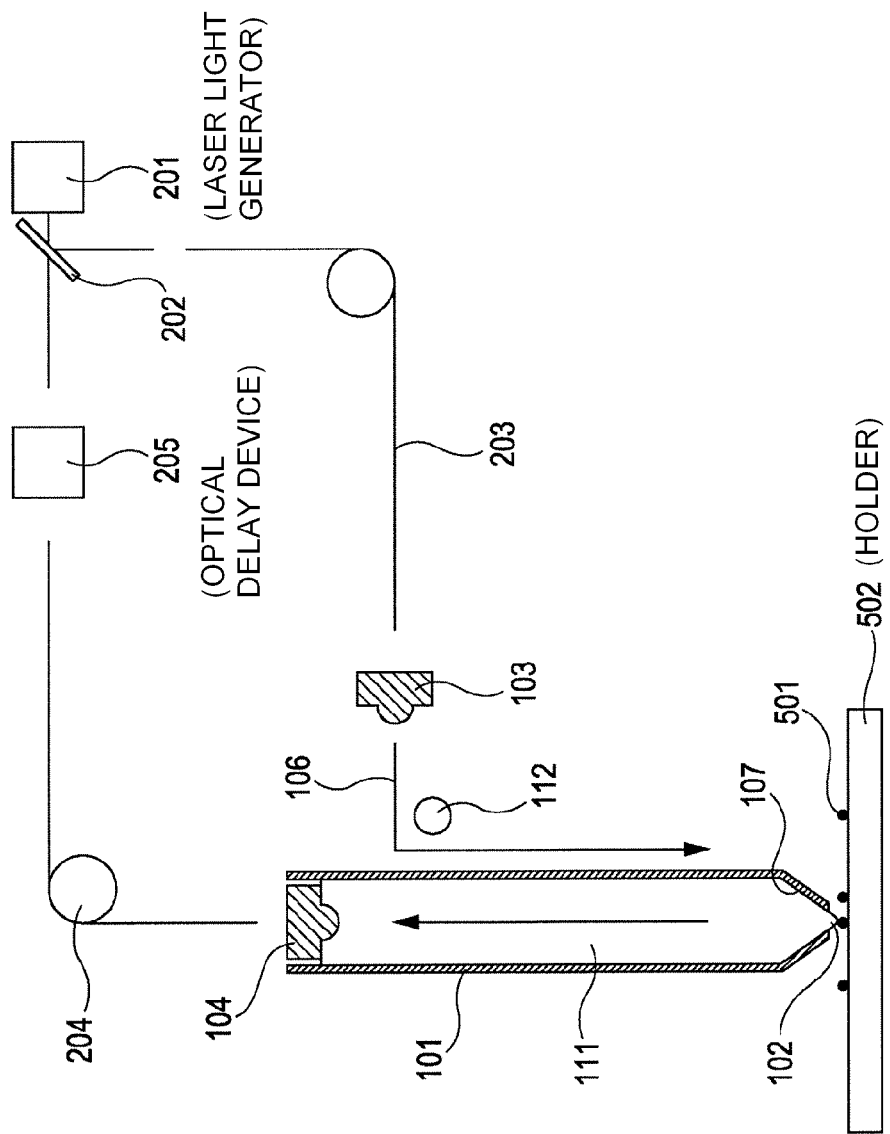
FIG. 5 is a sectional view showing the observation of a minute analyte with the probe and the near-field microscope according to the first example.

FIG. 5 shows another example to observe an analyte in the first example. In FIG. 5, reference numeral 501 denotes a minute analyte, for example, a DNA, which is in the submicron scale. Reference numeral 502 denotes a holder for the minute analyte 501, for example, a semiconductor wafer. Since the characteristic of molecular vibration in a DNA appears in the frequency region of the terahertz band, this example can be used, for example, to distinguish a plurality of DNAs with different structures by their characteristics of molecular vibration. Since the desired spatial resolution is nearly equal to the scale of the DNAs, the diameter of the minute aperture 102 suitable for observing each DNA is 300 nm.

Figure 6:
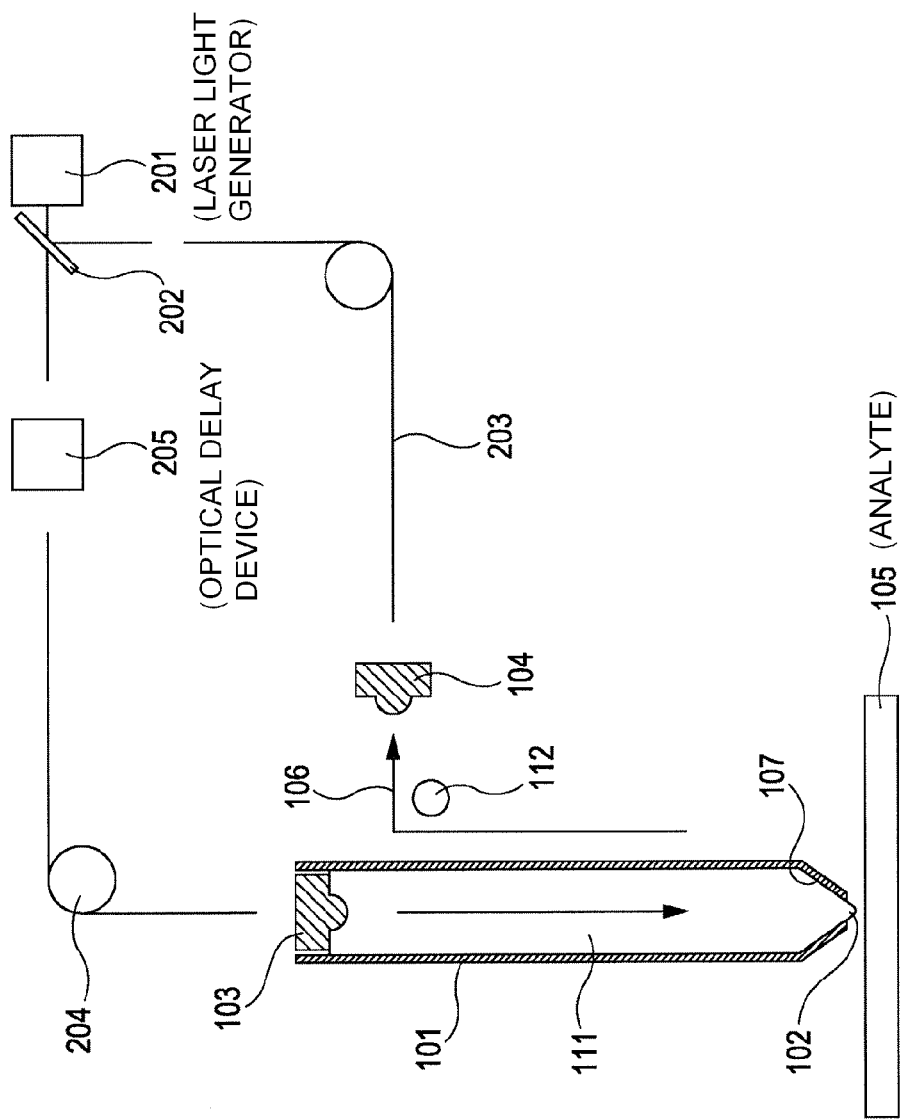
FIG. 6 is a sectional view showing a modification of the configuration of the probe and the near-field microscope according to the first example.

In the first example, the photoconductive antenna serving as the terahertz wave generator 103 is, as is well known, supplied with a bias voltage to generate a terahertz wave. In the photoconductive antenna serving as the terahertz wave detector 104, as is also well known, a current flowing into the photoconductive antenna is detected. If the operation of the terahertz wave generator 103 in FIG. 2 is exchanged for the operation of the terahertz wave detector 104 in FIG. 2, the high-frequency electrical signal 106 flows in the reverse direction. That is to say, the terahertz wave generator 103 in FIG. 2 functions as a terahertz wave detector, and the terahertz wave detector 104 in FIG. 2 functions as a terahertz wave generator, as shown in FIG. 6. The dielectric properties of the analyte can also be measured in this way. In FIG. 6, reference numeral 112 denotes the foregoing cross-wire terahertz wave coupling unit. The high-frequency electrical signal 106 propagating in the outer part of the circular waveguide 101 is directed to the detector 104 by the cross-wire terahertz wave coupling unit 112.

The above-described first example can simplify the apparatus and can provide a probe and a near-field microscope that have a comparatively high sensitivity in the frequency region from the millimeter waveband to the terahertz band.

Second Example

Figure 3:
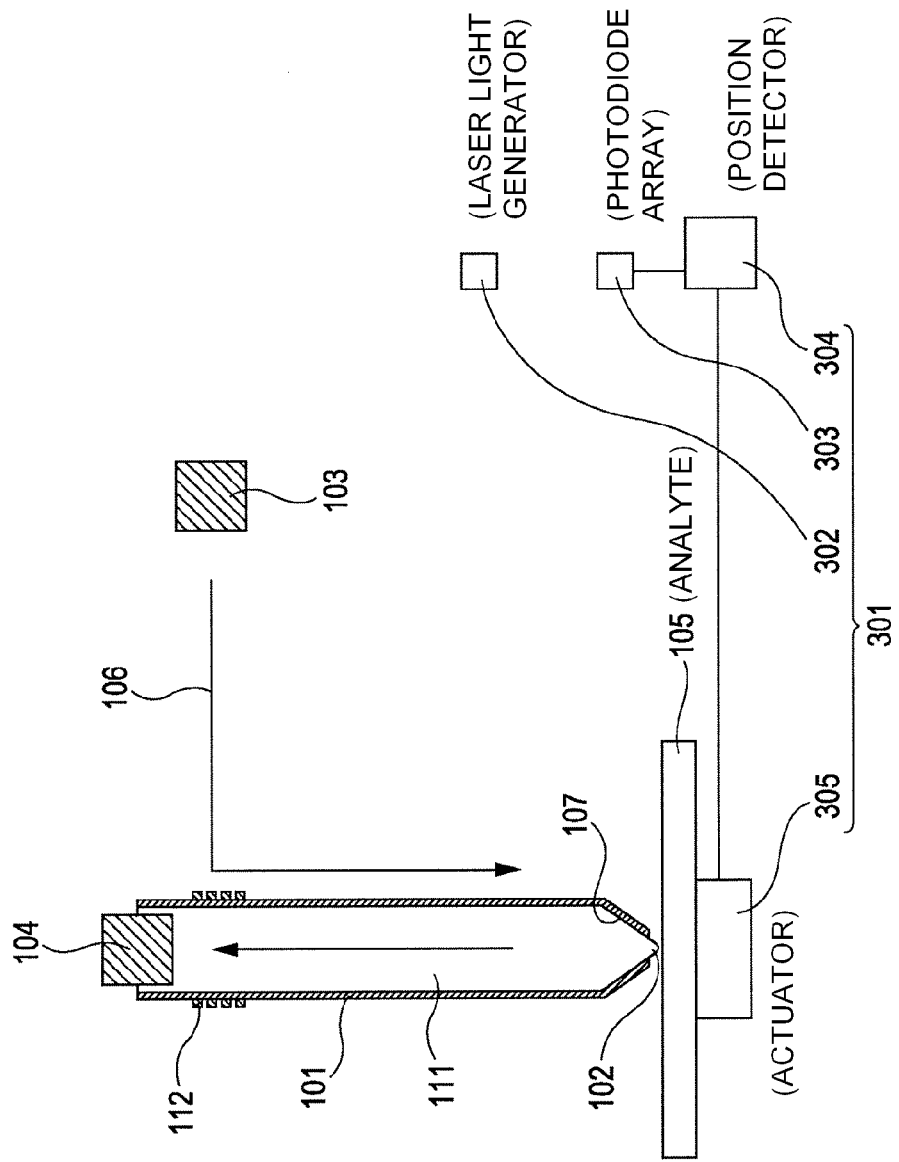
FIG. 3 is a sectional view showing the configuration of a probe and a near-field microscope according to a second example of the present invention.

FIG. 3 is a sectional view showing a second example of a probe and a near-field microscope according to the present invention. In FIG. 3, reference numeral 101 is a rectangular waveguide filled with a dielectric material 111, and reference numeral 102 denotes a minute aperture formed at the terminal end of the rectangular waveguide 101. Reference numeral 103 denotes a terahertz wave generator. In this example, the terahertz wave generator 103 is a continuous wave light source (a BWO, a quantum cascade laser, or a resonant tunneling diode). Reference numeral 104 denotes a terahertz wave detector. In this example, the terahertz wave detector 104 is a pyroelectric element. Reference numeral 106 denotes the flow of the terahertz wave due to this arrangement. In addition, in order to image an analyte 105 disposed near the minute aperture 102, this example includes a probe-position control system 301 configured to make the probe according to this example scan the analyte 105.

The probe-position control system 301 is configured using well-known methods. For example, as shown in FIG. 3, the system 301 includes a laser light generator 302, a photodiode array 303, a position detector 304, and an actuator 305 and feedback-controls the relative positional relationship between the minute aperture 102 and the analyte 105. Part of the light from the laser light generator 302 reflected by the side surface of the rectangular waveguide 101 is detected by the photodiode array 303. On the basis of the amount of displacement of the detected light, position information can be obtained. At this time, the relative position information between the minute aperture 102 and the analyte 105 is input into the position detector 304, and the actuator 305 corrects the displacement from a predetermined position.

The position detection using laser light enables a control on a submicron scale. In addition to the above probe position control system, in order to accurately maintain a constant distance between the minute aperture 102 and the analyte 105, a position control method using atomic force, tunneling current, or floating capacitance may be used. Thus, imaging can be achieved by obtaining and processing both the relative position between the minute aperture 102 and the analyte 105, and by the reflection of the terahertz wave from the analyte 105.

In this example, since a continuous wave light source is used as the terahertz wave generator 103, monochromaticity is comparatively high. In the case where the monochromaticity of the terahertz wave radiated from the terahertz wave generator 103 is high, the coupling efficiency can be further improved with a metal grating terahertz wave coupling unit 112 shown in FIG. 3 so as to further improve the S/N ratio (signal-to-noise ratio) of the detection signal.

This imaging is used, for example, for observing the carrier concentration distribution in a semiconductor wafer. The plasma frequency estimated from a typical carrier concentration of semiconductor wafers is located in the frequency region of the terahertz band. The complex dielectric constant changes drastically near the plasma frequency. Therefore, the probe and the near-field microscope of this example is used, for example, for observing the carrier concentration distribution in a semiconductor wafer with higher spatial resolution.

In this example, the rectangular waveguide 101 can be manufactured using the same method as described in the first example. The pyroelectric element 104 is comparatively small-sized and is, as shown in FIG. 3, fitted into the other terminal end of the rectangular waveguide 101. The metal grating terahertz wave coupling unit 112 can be manufactured through a well-known process including, for example, application of photoresist, development, and plasma etching.

Third Example

Figure 4:
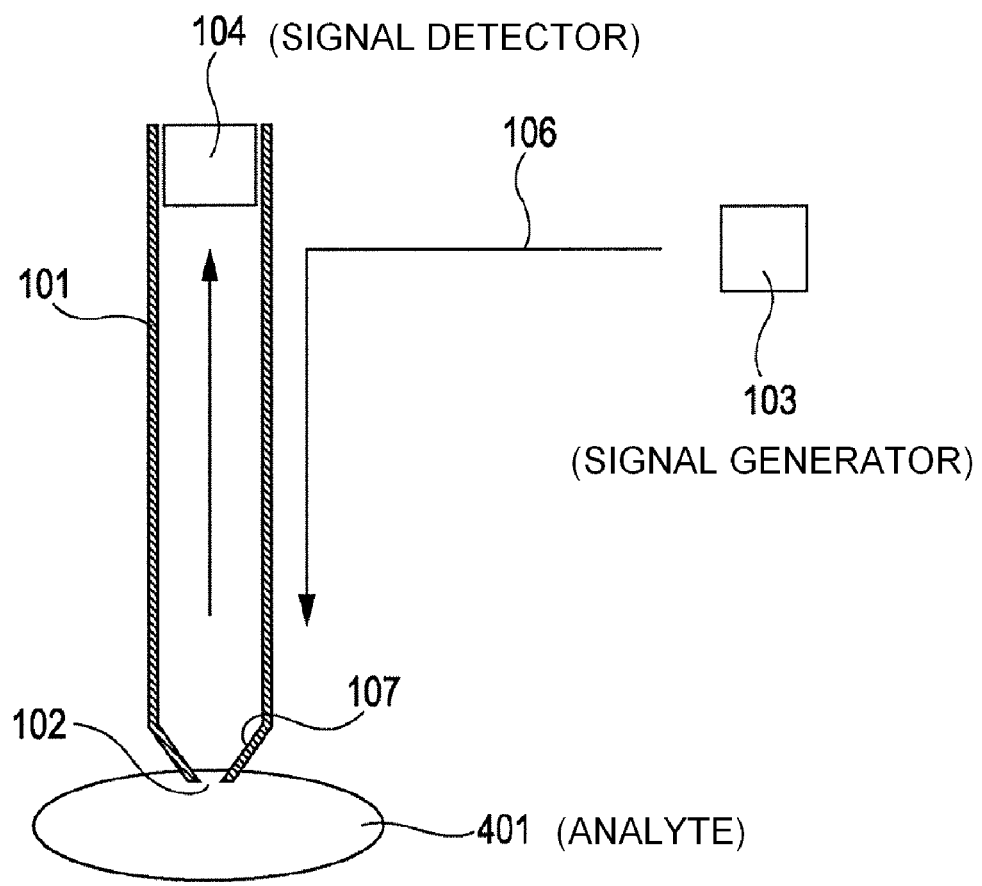
FIG. 4 is a sectional view showing the configuration of a probe and a near-field microscope according to a third example of the present invention.

FIG. 4 is a sectional view showing a third example of a probe and a near-field microscope according to the present invention. The third example shown in FIG. 4 is an example in which a tubular conductor 101 is inserted into an analyte 401 having an inner structure of the above-described embodiment of the present invention. Therefore, this example can measure not only the dielectric properties in the skin structure of the analyte 401 but also the dielectric properties of the inner structure of the analyte 401. The analyte 401 is preferably an object that does not make the coupling between the outer part and the inner part of the tubular conductor 101 through the minute aperture 102 too small. Therefore, the analyte 401 is preferably an object that does not have conducting properties. In addition, in order to prevent the decrease in sensitivity, the analyte 401 is preferably a dielectric material whose dielectric tangent (tan δ) is small (for example, 0.1 or less).

This example is used, for example, for observing the three-dimensional distribution of the dielectric properties in a rubber material. It is well known that when sulfur is added to a rubber material in order to cause cross-linking, the sulfur binds chemically to other molecules and effects a change in complex dielectric constant. The characteristic also appears in the frequency region of the terahertz band. The generator 103 preferably generates a high-frequency electrical signal at a frequency (or in a frequency region) at (or in) which the complex dielectric constant due to the chemical bond between sulfur and other molecules changes drastically. In this case, the contrast is improved. For example, if the probe is appropriately scanned or swept using the probe position control system described in the second example, the three-dimensional spatial distribution of the dielectric properties of the rubber material can be observed.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-073614 filed Mar. 17, 2006, which is hereby incorporated by reference herein in its entirety.

What is claimed is:

1. A probe comprising:
   a tubular conductor having an aperture at one end thereof;
   an electromagnetic wave transmitting unit for transmitting an electromagnetic wave, via said tubular conductor, to a position distant from the aperture; and
   an electromagnetic wave receiving unit for receiving an electromagnetic wave, via said tubular conductor, from the position distant from the aperture,
   wherein the electromagnetic wave transmitting unit is disposed at one of the inside and the outside of the tubular conductor,
   the electromagnetic wave receiving unit is disposed at the other of the inside and the outside of the tubular conductor,
   the size of the aperture is smaller than or equal to the wavelength of the electromagnetic waves,
   the electromagnetic waves transmitted and received at the outside and the inside of the tubular conductor are coupled through the aperture, and
   when an analyte to be observed is disposed so as to face the aperture, information of the analyte is obtained on the basis of a change in the coupling of the electromagnetic waves through the aperture.

2. The probe according to claim 1, further comprising a dielectric material inside the tubular conductor.

3. The probe according to claim 1, further comprising an electromagnetic wave coupling unit outside the tubular conductor, for regulating the efficiency of coupling the electromagnetic waves with the free space.

4. The probe according to claim 1, wherein the end of the tubular conductor having the aperture is tapered.

5. The probe according to claim 1, wherein the electromagnetic waves include part of the frequency region from 30 GHz to 30 THz.

6. A near-field microscope comprising the probe according to claim 1 and a position control system for controlling the relative positional relationship between the probe and the analyte.

7. An analyte observing method for obtaining information of an analyte using the probe according to claim 1, the method comprising the step of making an electromagnetic wave that is a traveling wave exist in the inner part of the tubular conductor.

8. An analyte observing method for obtaining information of an analyte using the probe according to claim 1, the method comprising the step of making an electromagnetic wave that is a standing wave exist in the inner part of the tubular conductor.

* * * * *